United States Patent
Sääski et al.

(10) Patent No.: US 7,146,686 B2
(45) Date of Patent: Dec. 12, 2006

(54) CASE STRUCTURE FOR SENSOR STRUCTURE ATTACHABLE TO AND DETACHABLE FROM A SHOE

(75) Inventors: Jarmo Sääski, Kempele (FI);
Veli-Pekka Putila, Oulu (FI); Janne Lindholm, Oulu (FI)

(73) Assignee: Polar Electro Oy, Kempele (FI)

( * ) Notice: Subject to any disclaimer, the term of this patent is extended or adjusted under 35 U.S.C. 154(b) by 22 days.

(21) Appl. No.: 10/873,753

(22) Filed: Jun. 22, 2004

(65) Prior Publication Data
US 2005/0166373 A1    Aug. 4, 2005

(30) Foreign Application Priority Data
Jan. 30, 2004   (FI) ................................. 20040143

(51) Int. Cl.
  *A45F 5/02*   (2006.01)
  *A45F 5/00*   (2006.01)
(52) U.S. Cl. .................. 24/3.7; 224/269; 224/929; 224/930
(58) Field of Classification Search .............. 24/3.1, 24/3.2, 3.5, 3.7, 3.8, 3.9, 3.12; 224/930, 224/269, 929
See application file for complete search history.

(56) References Cited

U.S. PATENT DOCUMENTS 3,157,927 A  * 11/1964  Roden ........................ 24/3.7
4,649,552 A    3/1987  Yukawa
5,097,997 A  *  3/1992  Kipnis et al. ................ 224/269
5,312,029 A  *  5/1994  Tuber ......................... 224/269
5,650,982 A    7/1997  Takenaka et al.
2002/0152645 A1  10/2002  Darley et al.
2003/0000053 A1   1/2003  Rooney et al.

FOREIGN PATENT DOCUMENTS

JP       2002214691    7/2002
WO       WO 88/04768   6/1988

* cited by examiner

Primary Examiner—Robert J. Sandy
(74) Attorney, Agent, or Firm—Hoffmann & Baron, LLP

(57) ABSTRACT

The invention relates to a case structure for a sensor structure attachable to and detachable from a shoe, the case structure comprising a case and an attachment arrangement for attaching the case to the shoe, the attachment arrangement comprising an attachment projection structure intended to attach the case to the shoe such that shoelaces remain between a bottom comprised by the case and the attachment projection structure below the bottom. The essential feature in the invention is that the attachment projection structure is a branched projection structure comprising a first projection branch and a second projection branch, and, between the projection branches, an intermediate area intended to enable the placing of the case structure in position even if the shoelaces were arranged to support a tongue of the shoe.

11 Claims, 5 Drawing Sheets

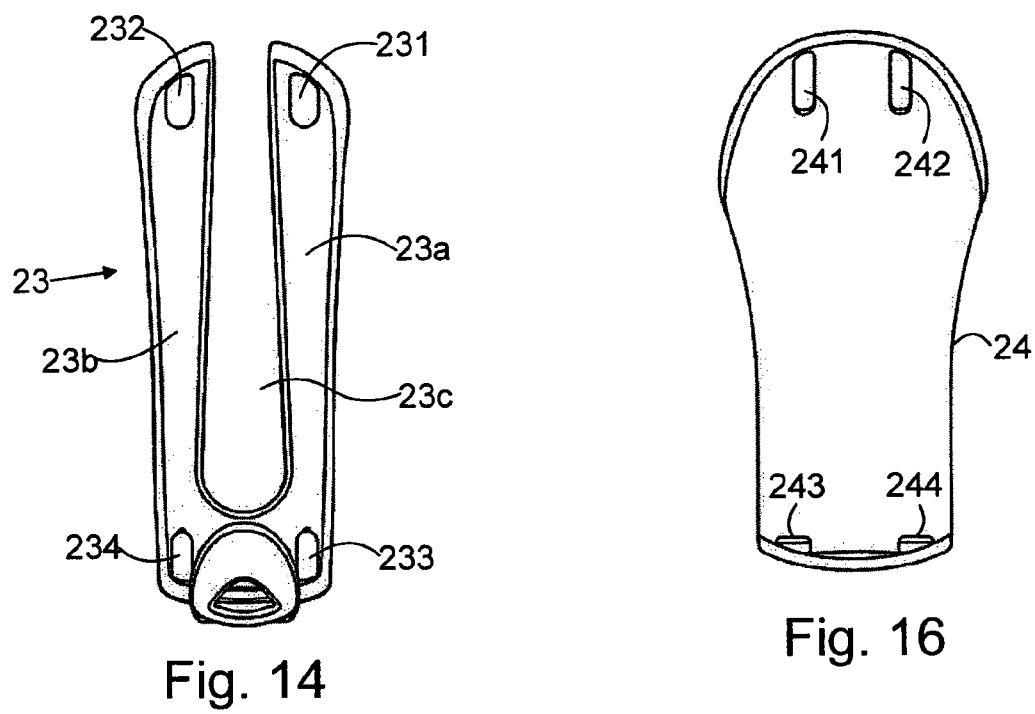
Fig. 14
Fig. 16
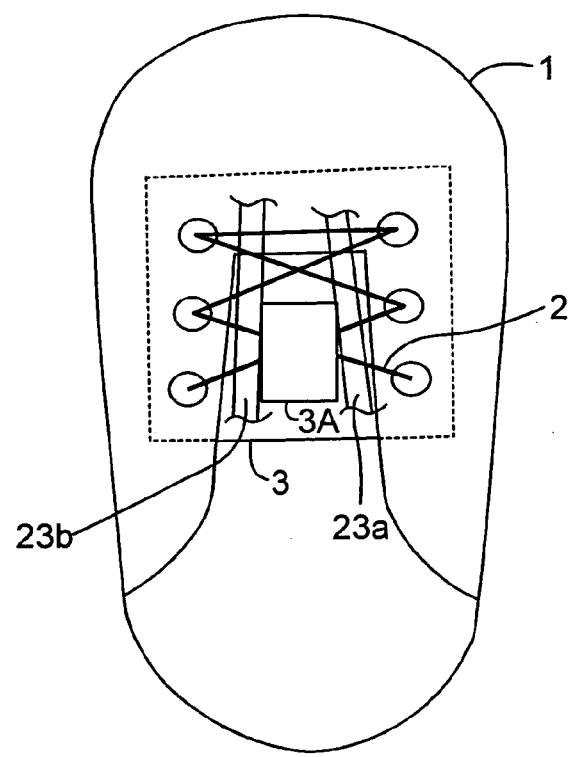
Fig. 17

CASE STRUCTURE FOR SENSOR STRUCTURE ATTACHABLE TO AND DETACHABLE FROM A SHOE

CROSS-REFERENCE TO RELATED APPLICATION

This application claims priority based on Finnish Patent Application No. 20040143, filed on Jan. 30, 2004.

The invention relates to a case structure for a sensor structure attachable to and detachable from a shoe, the case structure comprising a case and an attachment arrangement for attaching the case to the shoe, the attachment arrangement comprising an attachment projection structure intended to attach the case to the shoe such that shoelaces remain between a bottom comprised by the case and the attachment projection structure below the bottom.

BRIEF DESCRIPTION OF THE RELATED ART

Several factors can be measured of a person performing an exercise. In one measuring method, an encased sensor is located on top of the person's shoe, the sensor measuring the acceleration of the foot or the number of steps, for example. The encased sensor is placed on top of the shoelaces such that an attachment projection below the bottom of the case settles below the laces and the bottom of the case on top of the laces. The case structure of known acceleration sensors is such that the attachment projection structure below the case is a solid single-piece projection, which does not allow the sensor to be installed in the case structure on top of the shoe if the shoelaces are conveyed through a supporting loop on top of a tongue part in the shoe, since in this case the joint of the laces and the tongue part would prevent the propagation of the attachment projection structure below the laces. That is to say, a person using a laced sports shoe often wants to convey the laces along such a route that the laces pass through the supporting loop of the tongue of the shoe, facilitating the putting on of the shoe, since the tongue of the shoe is already in an upper position, i.e. supported by the laces immediately below the laces. The single-part attachment projection structure of known solutions is problematic also because a single-part structure does not properly fit or settle on top of the arched tongue in the shoe on top of the arched ankle area.

SUMMARY OF THE INVENTION

The object of the invention is to provide a new type of case structure for a sensor structure attachable to or detachable from a shoe and enabling better adaptation to the needs of the user than previous solutions.

This is achieved with the case structure of the invention, which is characterized in that the attachment projection structure is a branched projection structure comprising a first projection branch and a second projection branch, and, between the projection branches, an intermediate area intended to enable the placing of the case structure in position even if the shoelaces were arranged to support a tongue of the shoe.

Preferred embodiments of the invention are described in the dependent claims.

The invention is based on the projection structure attaching the case of the case structure to the shoe being implemented in a manner enabling easy attachment to the shoe irrespective of whether or not the tongue of the shoe is supported by the laces. A shoe refers to a conventional laced shoe, but also to a skate, ski boot or other laced footwear or a laced sportswear comprising a shoe-like structure. For example, skates, roller-skates and ski boots are in a way shoes provided with a blade, wheels or a binding means.

The case structure of the invention provides a plurality of advantages. The invention enables the attachment of an encased sensor to a shoe on top of the laces such that the attachment projection structure is able to propagate below the laces when being placed in position even if the laces support the tongue of the shoe. Due to its better attachment projection structure, the case structure of the invention also settles in position more firmly on top of the arched tongue in the shoe on top of the arched ankle area.

BRIEF DESCRIPTION OF THE DRAWINGS

In the following, preferred embodiments of the invention will be described in detail with reference to the accompanying drawings, in which FIG. 14 shows the structure of FIG. 13 as seen from the direction of the case, FIG. 16 shows the second locking structure of FIG. 15 seen from the direction of the top surface of the case towards the bottom of the second locking structure, FIG. 17 shows the routing of shoelaces for supporting the tongue of the shoe.

DETAILED DESCRIPTION OF THE PREFERRED EMBODIMENTS

Figure 1:
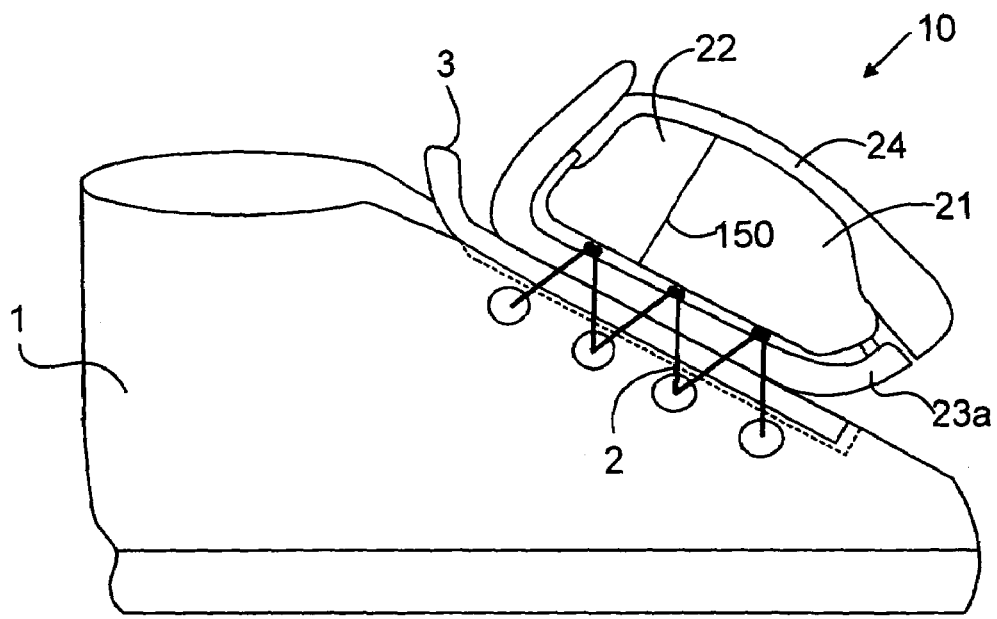
FIG. 1 shows a sensor structure arranged on top of a shoe, FIG. 2 schematically shows the case parts of a case together with sensor parts inside the case.

With reference to the figures, the invention relates to a case structure 20, 21 to 24 of a sensor structure 10 attachable to and detachable from a shoe 1. The shoe 1 is a sports shoe or another shoe provided with laces 2. The shoe refers to a conventional laced shoe, but also to a skate, roller-skates or a ski boot or other laced footwear or sportswear provided with a laced shoe-like structure. For example, skates, roller-skates and ski boots are in a way shoes provided with a blade, wheels or a binding means.

The case structure 21 to 24 comprises a case 21 to 22, i.e. a first case part 21 of the case and a second case part 22 of the case, the case parts providing a case when interconnected. In addition, the case structure 20 comprises an attachment arrangement 23, 24 for attaching the case 21 to 22 to the shoe 1. The parts 23, 24 also interlock the case parts 21, 22. The material of the case structure is polyamide, for example.

Figure 2:
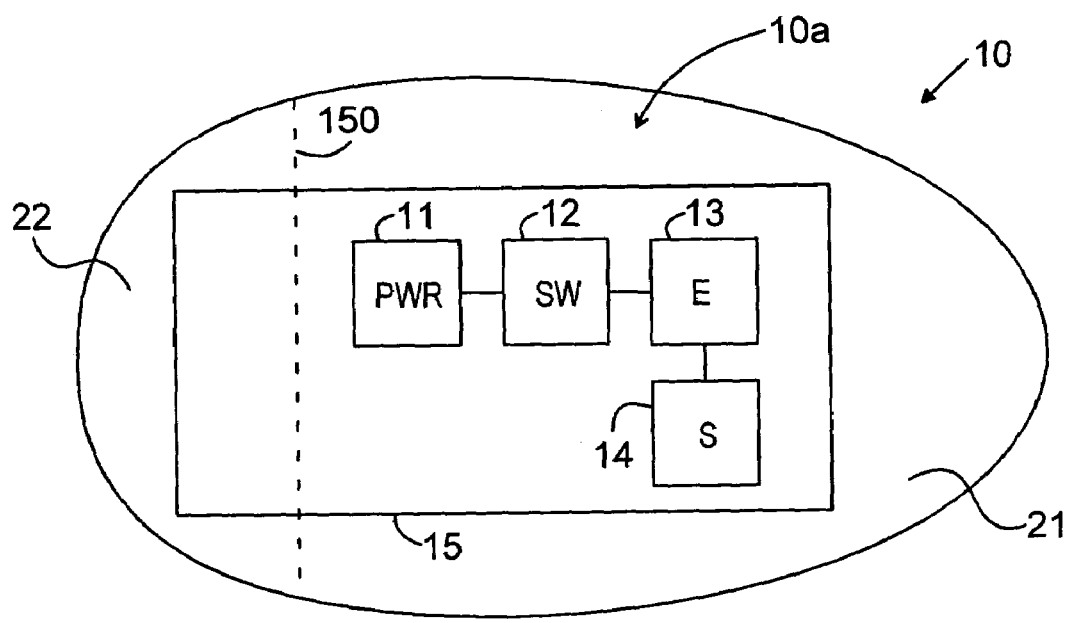
Figure 3:
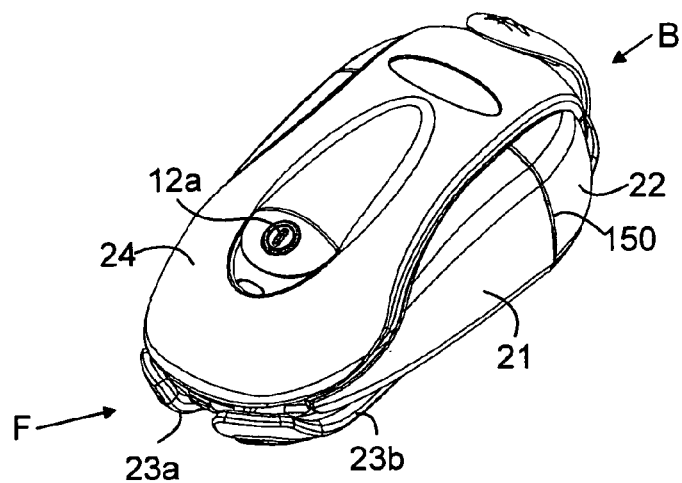
FIG. 3 shows the case structure as seen obliquely from the top from the direction of the front end.
Figure 4:
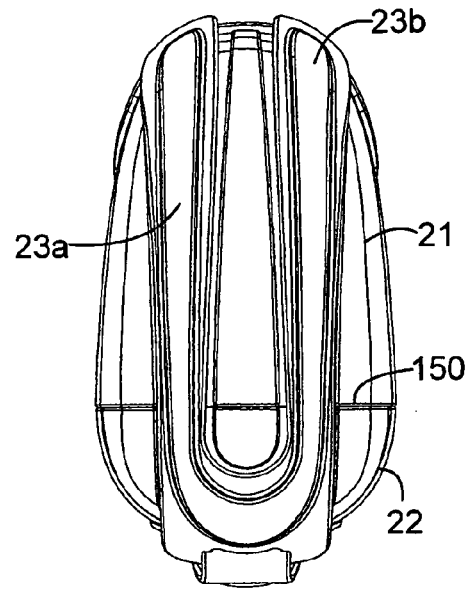
FIG. 4 shows the case structure as seen perpendicularly from the side of the bottom of the case structure.
Figure 5:
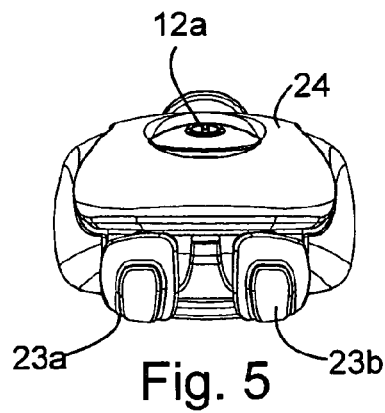
FIG. 5 shows the case structure as seen perpendicularly towards the front end.
Figure 6:
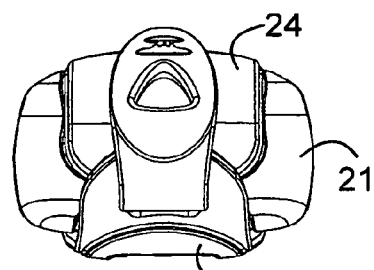
FIG. 6 shows the case structure as seen perpendicularly towards the rear end.
Figure 7:
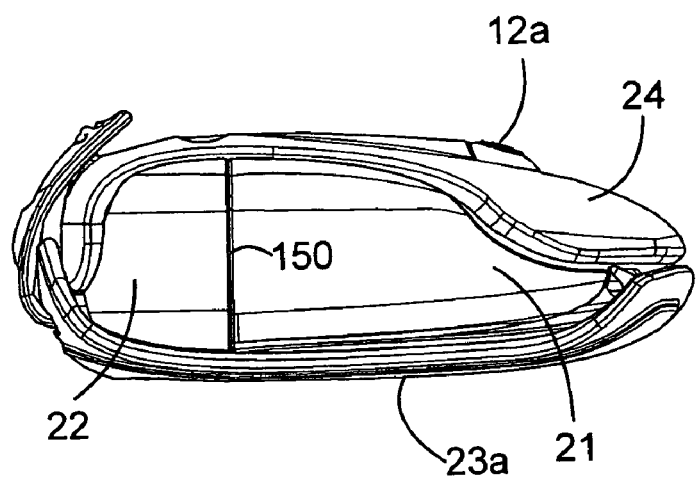
FIG. 7 shows the case structure as seen perpendicularly from the side.
Figure 8:
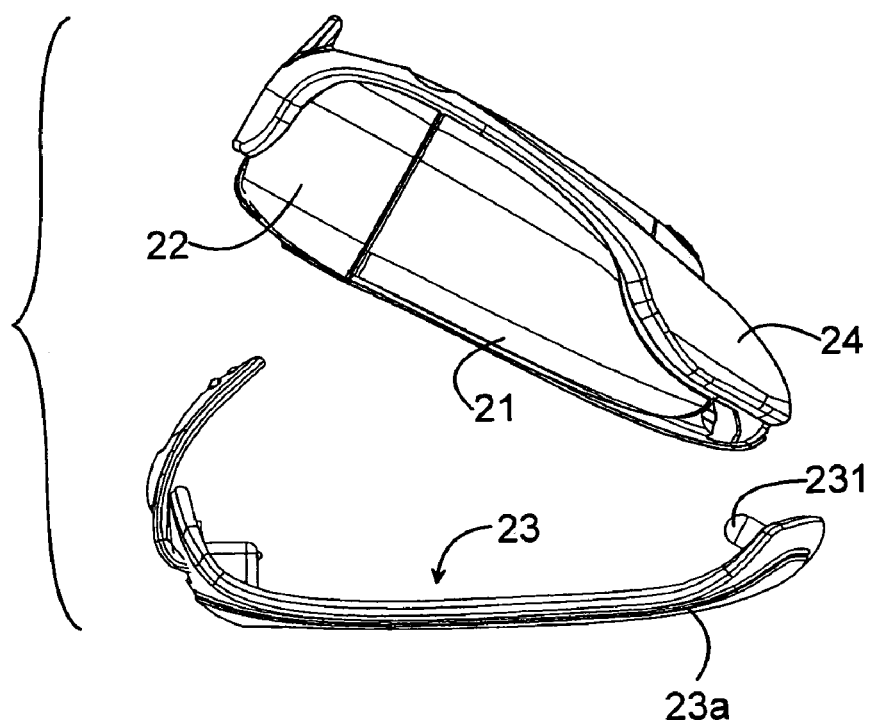
FIG. 8 shows the structures of FIG. 7 partly detached.

With special reference to FIG. 2, in this connection, the term sensor 10a refers to the structural parts in the case structure, i.e. in practice, encased in the case 21 to 22 of the case structure. A sensor structure refers to the entity constituted by the case structure and the parts encased therein, i.e. the sensor.

Figure 9:
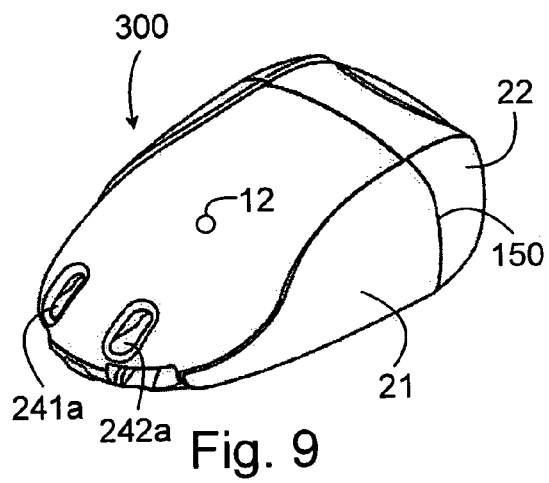
FIG. 9 shows a case composed of two case parts seen obliquely from the top from the direction of the front end.
Figure 10:
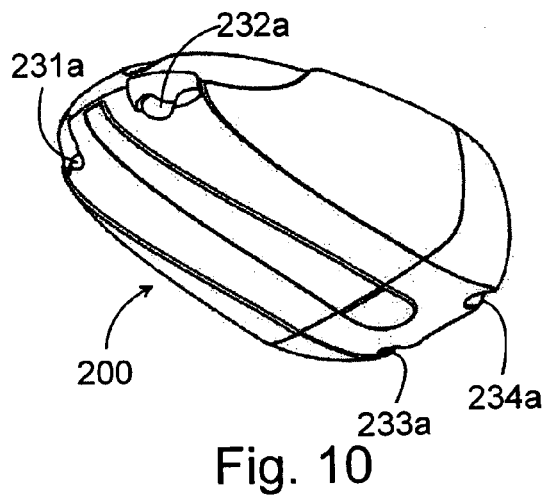
FIG. 10 shows a case composed of two case parts seen obliquely from below from the side of the bottom.
Figure 11:
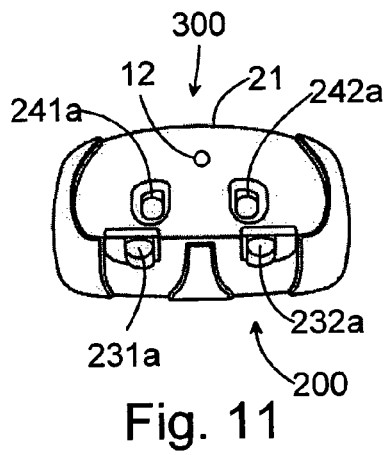
FIG. 11 shows the case as seen perpendicularly from the direction of the front end.
Figure 12:
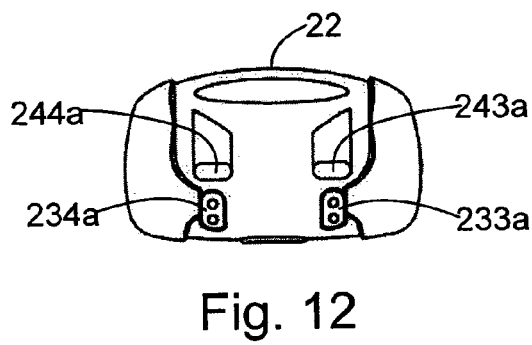
FIG. 12 shows the case as seen perpendicularly from the direction of the rear end.

In accordance with FIG. 2, the sensor 10a comprises a power source 11, a switch 12, an electronics unit 13 and a sensor element 14. The switch 12 can be seen also in FIGS. 9 and 11. FIGS. 3, 5, 7 and 8 show a thinned wall 12a of the second locking means, i.e. the upper locking means 24, or another structure allowing the switch 12 comprised by the case to be opened through it. In FIG. 2, the electronics unit 13 controls the operation, modifying and interpreting the measuring results of a sensor element 14. The switch 12 is used to switch the power source for use by the electronics unit. The sensor element 14 may be for instance a semiconductor acceleration sensor, a piezo or of the MEMS type (Micro-Electro-Mechanical System). The measuring data of the sensor structure can be transferred for instance by means of a radio connection or magnetic telemetry for instance to a wrist receiver, which may a heart rate monitor wristband, for example. The sensor may also comprise a display. Acceleration measurements can be used for instance to find out the speed, the distance, the number of steps, the length of steps and the path of the step.

Figure 13:
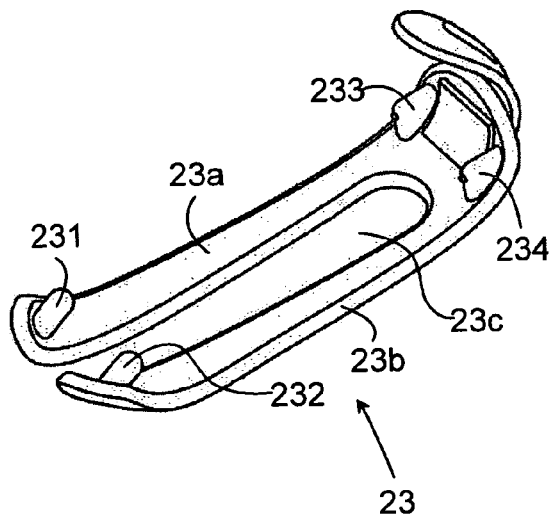
FIG. 13 shows a locking projection structure also comprising the structural parts of a first locking structure.
Figure 15:
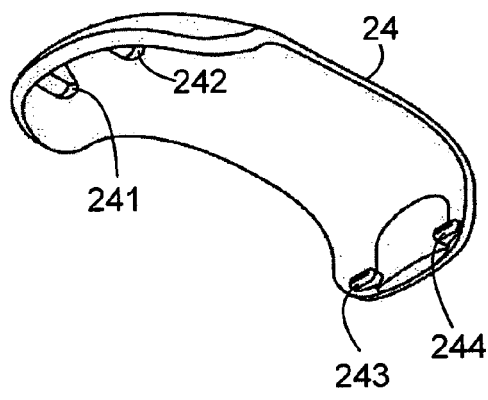
FIG. 15 shows an upper locking structure, i.e. a second locking structure seen obliquely from below.

FIG. 2 also shows that the parts encased in the case structure are supported by a common support element 15 also comprised by the sensor, the structural parts 11 to 15 constituting a plug-in type of integrated entity, which clarifies the service measures of the sensor structure, since all structural parts 11 to 15 can be removed from the case 21 to 22 and placed into the case 21 to 22 as a whole. Of the parts of the case structure, FIG. 2 shows only the case, i.e. the joined case parts 21 to 22. The other two parts of the case structure, i.e. the parts 23, 24 visible in FIG. 13 and 15, are not shown in FIG. 2.

A limit 150 between the first case part 21 and the second case part 22 is the limit in the direction between a top surface 300 of the case and a bottom surface 200 of the case when the case structure is viewed from the side. As regards service measures, this provides an easy way of operation, i.e. the end can be opened; i.e. the case structure can be opened from the side of the rear end B of the case in the example of the figures. In addition, better water tightness is achieved, since the area of the limit 150 to be sealed in the shorter direction, i.e. the transverse direction, is smaller as compared with the longitudinal direction of the case structure. The transverse limit 150 also enables the use of the projection structure piece 23 by means of auxiliary parts 231 to 234 also for pressing the case parts 21 and 22 against one another, i.e. locking against one another.

With particular reference to FIGS. 1, 3 to 8, and 14 to 15, the attachment arrangement comprises an attachment projection structure 23, 23a, 23b. The attachment projection structure is intended to attach the case to the shoe such that the shoelaces 2 remain between the bottom 200 comprised by the case 21 to 22 and the attachment projection structure 23, 23a, 23b under the bottom.

The attachment projection structure 23 is a branched projection structure 23 comprising a first projection branch 23a and a second projection branch 23b, an intermediate area 23c remaining between said projection branches and being intended to enable the placement of the case structure onto the shoe even if the shoelaces 2 were arranged to support the tongue 3 of the shoe by means of a tongue suspension member 3A, i.e. a supporting loop 3A, for example. This can be seen in FIG. 17. The case structure is placed onto the shoe by first placing the projections of the projection structure 23, 23a, 23b shown in FIGS. 13 to 14 below the shoelaces 2 onto the tongue 3 of the shoe, whereupon the other parts 21, 22, 24 of the case structure are pressed into the projection structure piece 23 in the manner shown in FIG. 8.

The case 21 to 22 and, naturally, the case structure, comprise a front end F and a rear end B. In order for the sensor structure placed in position on top of the shoe, i.e. the case structure including the sensor, to remain in position, in a preferred embodiment the case structure is such that the width of the intermediate area 23c between the projection branches 23a, 23b of the attachment projection structure 23 is convergent from the rear end of the case towards the front end of the case. This is shown particularly in FIGS. 14 and in FIG. 4, too. To implement the converging intermediate area between the projection branches of the attachment projection structure, in a preferred embodiment the implementation is such that the distance between the projection branches 23a, 23b is shorter at the front end of the case than at the rear end of the case. Due to the convergence, the inner edges of the projection branches 23a, 23b hit the joint of the supporting loop of the tongue and the laces, thus preventing a separating movement.

The parts of the case 21 to 22 of the case structure, i.e. the first case part 21 and the second case part 22, are provided in order to enable the opening and closing of the case. Because of the two interconnected parts 21 and 22, the attachment arrangement for fastening the case to the shoe 1 comprises, not only the projection structure, but also locking means for interlocking the case parts.

In a preferred embodiment the case structure is such that the attachment projection structure 23, 23a, 23b comprised by the attachment arrangement is in the same piece as one or more locking means 231 to 234 comprised by the attachment arrangement. The locking means 231 to 232 are positioning members, such as positioning pegs, at the ends of the projection branches 23a, 23b of the attachment projection structure 23, which are positioned in nests 231a, 232a in the case part 21 of the case or in other positioning counterparts 231a, 232a. Accordingly, the positioning members 231 to 232 are at the front end F of the case. The locking means 233 to 234 are positioning members, such as positioning pegs 233 to 234, in the attachment projection structure 23 on the side of the rear end B of the case, and they settle in nests 233a, 234a in the second case part 22 of the case or in other positioning counterparts 233a, 234a. Accordingly, the locking means 231 to 234, i.e. the positioning pegs 231 to 234, for example, are the same integrated piece as the attachment projection structure 23, 23a, 23b, which reduces the number of parts and enables the performance of two tasks with one structure.

A corresponding locking positioning is provided between the second locking structure 24 and the case parts of the case between the pegs 241 to 244 of the locking structure 24 and the nests 241a to 244a of the case.

In this case, the second locking structure 24, 241 to 244 comprises, at the front end F of the case, a positioning structure 241, 242 for the positioning counterpart structure 241a, 242a comprised by the first case part. At different sides of the boundary line 150 between the case parts, the second locking structure 24, 241 to 244 comprises, at the rear end B of the case, a positioning structure 243 to 244 for the positioning counterpart structure 243a, 244a comprised by the second case part 22.

The arcuate parts 23, 24 are flexible, allowing them to be placed in position around the case 21, 22. The structural parts 23, 231 to 234, the structural parts 24, 241 to 244, and the nests 231a to 234a, 241a to 244a of the case provide a reliable locking between the case parts 21, 22 of the case.

Although the invention is described above with reference to the example according to the attached drawings, it is apparent that the invention is not limited thereto, but can be modified in a plurality of ways within the scope of the appended claims.

What is claimed is:

1. A case structure for a sensor structure attachable to and detachable from a shoe, the shoe comprising shoelaces, the case structure comprising a case and an attachment arrangement for attaching the case to the shoe, the attachment arrangement comprising an attachment projection structure intended to attach the case to the shoe such that the shoelaces of the shoe remain between a bottom comprised by the case and the attachment projection structure below the bottom, wherein the attachment projection structure is a branched projection structure comprising a first projection branch and a second projection branch, and, between the projection branches, an intermediate area intended to enable the placing of the case structure in position even if the shoelaces were arranged to support a tongue of the shoe, the case comprising a first case part and a second case part to enable the opening and closing of the case, the attachment arrangement adapted to attach the case to the shoe comprising, not only the projection structure, but also locking means for interlocking the case parts.

2. A case structure as claimed in claim 1, wherein the case comprises a front end and a rear end and that the width of the intermediate area between the projection branches of the attachment projection structure is convergent from the rear end of the case towards the front end of the case.

3. A case structure as claimed in claim 2, wherein, to implement the converging intermediate area between the projection branches of the attachment projection structure, the distance between the projection branches is shorter at the front end of the case than at the rear end of the case.

4. A case structure as claimed in claim 1, wherein a limit between the first case part and the second case part is the limit in the direction between a top surface of the case and a bottom surface of the case when the case structure is viewed from the side.

5. A case structure as claimed in claim 1, wherein the attachment projection structure comprised by the attachment arrangement is in the same piece as at least some of the locking means comprised by the attachment arrangement.

6. A case structure as claimed in claim 5, wherein a locking projection structure is in the same piece as the first locking structure on the side of the bottom surface of the case.

7. A case structure as claimed in claim 1, wherein the locking means for interlocking the case parts comprises a first locking structure and a second locking structure, and that the first locking structure is intended particularly for the side of the bottom surface of the case and the second locking structure is intended particularly for the side of the top surface of the case, and that the locking structures at both the front end and the rear end of the case extend towards one another thus constituting an interlocking of the case parts of the case around the case by the locking structures and the positioning supports between the case.

8. A case structure as claimed in claim 7, wherein the first locking structure comprises, at the front end of the case, a positioning structure for a positioning counterpart structure comprised by the first case part, and at different sides of a boundary line between the case parts, the first locking structure comprises, at the rear end of the case, a positioning structure for a positioning counterpart structure comprised by the second case part.

9. A case structure as claimed in claim 8, wherein the second locking structure comprises, at the front end of the case, a positioning structure for the positioning counterpart structure comprised by the first case part, and at different sides of the boundary line between the case parts, the second locking structure comprises, at the rear end of the case, a positioning structure for the positioning counterpart structure comprised by the second case part.

10. A case structure as claimed in claim 7, wherein the second locking structure comprises, at the front end of the case, a positioning structure for a positioning counterpart structure comprised by the first case part, and at different sides of the boundary line between the case parts, the second locking structure comprises, at the rear end of the case, a positioning structure for the positioning counterpart structure comprised by the second case part.

11. A case structure as claimed in claim 7, wherein a locking projection structure is in the same piece as the first locking structure on the side of the bottom surface of the case.

* * * * *